(12) United States Patent
Ishikubo et al.

(10) Patent No.: US 8,496,919 B2
(45) Date of Patent: Jul. 30, 2013

(54) COSMETIC COMPOSITION AND HAIR WASH

(75) Inventors: Akira Ishikubo, Yokkaichi (JP); Shoya Yoda, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 13/208,681

(22) Filed: Aug. 12, 2011

(65) Prior Publication Data

US 2011/0294773 A1 Dec. 1, 2011

Related U.S. Application Data

(63) Continuation of application No. PCT/JP2010/052549, filed on Feb. 19, 2010.

(30) Foreign Application Priority Data

Feb. 20, 2009 (JP) ................................ 2009-038093

(51) Int. Cl.
*A61K 8/81* (2006.01)
*A61K 8/49* (2006.01)
*A61K 8/02* (2006.01)
*A61Q 5/12* (2006.01)

(52) U.S. Cl.
USPC ............. 424/70.17; 424/401; 424/70.27; 424/70.16; 424/70.22; 424/70.28; 510/123; 526/303.1

(58) Field of Classification Search
None
See application file for complete search history.

(56) References Cited

U.S. PATENT DOCUMENTS

| 2003/0202952 A1 | 10/2003 | Wells et al. |
| 2007/0167593 A1 * | 7/2007 | Yoda et al. ................. 526/303.1 |
| 2008/0206355 A1 | 8/2008 | Schwartz et al. |

FOREIGN PATENT DOCUMENTS

| JP | 55-116800 | 9/1980 |
| JP | 2005/072685 | 8/2005 |
| JP | 2005-524689 | 8/2005 |
| JP | 2005-314615 | 11/2005 |
| JP | 2005-336387 | 12/2005 |
| WO | 03/088940 | 10/2003 |

OTHER PUBLICATIONS

International Search Report in PCT/JP10/52549 issued May 25, 2010 filed Feb. 29, 2010.
Chinese Office Action issued Aug. 3, 2012 in Patent Application No. 201080005546.6 with English Translation.

* cited by examiner

*Primary Examiner* — Rachael E Bredefeld
(74) *Attorney, Agent, or Firm* — Oblon, Spivak, McClelland, Maier & Neustadt, L.L.P.

(57) ABSTRACT

To provide a cosmetic composition and a hair wash which are excellent in metal pyrithione salt persistence after washing with a washing liquid containing a surfactant, etc.

A cosmetic composition and a hair wash, which comprise a copolymer and a metal pyrithione salt, wherein the copolymer contains constituting units corresponding to a cationic vinyl monomer of a specific structure and constituting units corresponding to a nonionic vinyl monomer of a specific structure.

8 Claims, No Drawings

COSMETIC COMPOSITION AND HAIR WASH

TECHNICAL FIELD

The present invention relates to a cosmetic composition and a hair wash, which comprise a copolymer of a specific structure and a metal pyrithione salt.

BACKGROUND ART

It is already well known to incorporate a metal pyrithione salt as represented by zinc pyrithione in a cosmetic composition, and when it is incorporated in a hair wash such as a shampoo, it is possible to effectively control formation of dandruff. It is known that such an anti-dandruff effect is brought about by the metal pyrithione salt which remains on the scalp or hair after washing, and its persistence in the washing process is substantially influential over such an effect. Therefore, a cosmetic composition showing a high persistence of a metal pyrithione salt at the time of washing is desired.

Heretofore, Patent Document 1 has reported on e.g. a shampoo composition wherein anti-dandruff particle persistence is improved by incorporating a specific cationic polysaccharide polymer.

PRIOR ART DOCUMENT

Patent Document

Patent Document 1: JP-A-2005-524689

DISCLOSURE OF INVENTION

Technical Problem

However, the anti-dandruff particle persistence shown in Patent Document 1 was not sufficient, and a further improvement in the anti-dandruff effect has been desired.

Further, it is extremely difficult to simultaneously attain letting a hardly water-soluble dispersed material such as a metal pyrithione salt having an anti-dandruff effect stay on the hair and removing dirt such as oil and dust from the hair or scalp, which is the intended purpose of the hair wash. Further, in a case where a conventional polymer as disclosed in Patent Document 1 was used for a cosmetic application, the effect for adsorption of a metal pyrithione salt such as zinc pyrithione was not sufficient.

As a method to overcome such a problem, it is conceivable to incorporate a large amount of an anti-dandruff agent such as a metal pyrithione salt, particularly zinc pyrithione, to the hair wash, but such a method is likely to bring about deterioration of the touch such as smoothness after the use, by the incorporation of a large amount of the anti-dandruff agent, or is likely to lead to environmental pollution such that a waste liquid containing a large amount of the anti-dandruff agent is discharged after the use of the hair wash.

It is an object of the present invention to solve such a problem and to provide a cosmetic composition which is capable of improving the metal pyrithione salt persistence after washing by a washing liquid containing a surfactant, etc. and which is capable of exhibiting a sufficient anti-dandruff effect by using only a small amount of a metal pyrithione salt. In addition, it is an object of the present invention to provide a hair wash which is made of such a composition and which is excellent in both the anti-dandruff effect and the washing property to remove dirt such as oil and dust from the hair or scalp and is also excellent in the touch such as smoothness after the use.

Solution to Problem

In view of the above problem, the present inventors have conducted an extensive study and as a result, have found that when a polymer having a specific amount of a cationic group and a specific amount of a hydroxy group and/or an amide group having only a nonionic substituent (hereinafter these groups may be referred to as functional groups), is incorporated, a metal pyrithione salt, particularly zinc pyrithione, exhibits a high residual effect. Further, it has been found that a cosmetic composition obtained by blending a metal pyrithione salt and a copolymer containing constituting units corresponding to a cationic vinyl monomer of a specific structure and constituting units corresponding to a nonionic vinyl monomer of a specific structure, exhibits a high metal pyrithione salt persistence. Thus, the present invention has been accomplished.

Thus, the present invention provides the following (i) to (v).

(i) A cosmetic composition comprising a cationic polymer and a metal pyrithione salt, wherein the cationic polymer has a cationic group and at least one group selected from a hydroxy group and an amide group having only a nonionic substituent; the amount of the cationic group is from 0.1 to 10.0 meq/g; at least one of the amount of the hydroxy group being from 1.5 to 20.0 meq/g and the amount of the amide group having only a nonionic substituent being from 1.5 to 10.0 meq/g, is satisfied; and when the cosmetic composition is used as a hair wash, the amount of adsorption of the metal pyrithione salt is at least 20 μg/g on at least one of untreated hair and damaged hair.

(ii) A cosmetic composition comprising a copolymer (1) and a metal pyrithione salt, wherein the copolymer contains constituting units corresponding to a cationic vinyl monomer (A) represented by the following formula (I) and constituting units corresponding to a nonionic vinyl monomer (B) represented by the following formula (II) and/or (III); the proportion of the constituting units corresponding to the cationic vinyl monomer (A) is from 10 to 80 wt % to the total constituting units constituting the copolymer; and the weight average molecular weight of the copolymer is from 10,000 to 2,000,000:

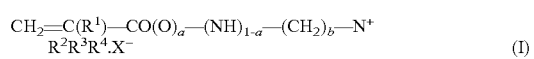
$$CH_2=C(R^1)-CO(O)_a-(NH)_{1-a}-(CH_2)_b-N^+R^2R^3R^4.X^- \quad (I)$$

(wherein $R^1$ is a hydrogen atom or a methyl group, each of $R^2$ and $R^3$ which are independent of each other, is a $C_{1-24}$ alkyl group, a $C_{1-24}$ aryl group or a $C_{1-24}$ aralkyl group, $R^4$ is a hydrogen atom, a $C_{1-24}$ alkyl group, a $C_{1-24}$ aryl group, a $C_{1-24}$ aralkyl group or $-CH_2-CH(OH)-CH_2-NR^5R^6R^7Y$, each of $R^5$ to $R^7$ which are independent of one another, is a $C_{1-24}$ alkyl group, a $C_{1-24}$ aryl group or a $C_{1-24}$ aralkyl group, each of $X^-$ and $Y^-$ which are independent of each other, is an anion, a is 0 or 1, and b is an integer of from 1 to 10)

$$CH_2=C(R^8)-CO(O)-X-H \quad (II)$$

(wherein $R^8$ is a hydrogen atom or a methyl group, and X is a bivalent linking group containing at least two hydroxy groups)

$$CH_2=C(R^9)-CO-NR^{10}R^{11} \quad (III)$$

(wherein $R^9$ is a hydrogen atom or a methyl group, and each of $R^{10}$ and $R^{11}$ which are independent of each other, is a hydrogen atom, a $C_{1-4}$ alkyl group or a $C_{1-4}$ hydroxyalkyl group).

(iii) The cosmetic composition according to the above (i) or (ii), wherein the metal pyrithione salt is zinc pyrithione.

(iv) The cosmetic composition according to any one of the above (i) to (iii), which further contains an anionic surfactant.

(v) A hair wash employing the cosmetic composition as defined in any one of the above (i) to (iv).

Advantageous Effects of Invention

It is known that a metal pyrithione salt effectively prevents dandruff. By using e.g. a hair wash having a metal pyrithione salt incorporated, it is permitted to stay on the hair thereby to exhibits the effect. The more the residual amount, the higher the anti-dandruff effect. The cosmetic composition of the present invention is excellent particularly in the metal pyrithione salt persistence after washing by a washing liquid containing a surfactant, etc. Thus, it is possible to exhibit a sufficient anti-dandruff effect by using only a small amount of the metal pyrithione salt.

Especially in a case where the cosmetic composition of the present invention is used as a washing liquid, it is possible to provide a washing liquid which is excellent in both the anti-dandruff effect and the washing property to remove dirt such as oil and dust from the body, particularly from the hair or scalp and which is excellent in the touch such as smoothness after the use.

DESCRIPTION OF EMBODIMENTS

Now, the present invention will be described in detail with reference to its embodiments, as the following description of the constituting elements relates to typical examples of embodiments of the present invention, it should be understood that the present invention is by no means thereby restricted.

In this specification, the "cationic group" means a functional group containing a positively charged atom such as nitrogen of a quaternary amine, and it may be in the form of a salt or in a state ionized in a solution. Further, the "cationic monomer" and the "cationic polymer" mean a monomer and polymer containing a positively charged atom, respectively. Further, the "nonionic monomer" means an electrically neutral monomer not containing an atom having an electric charge. Further, "cationic" used in the above "cationic group", "cationic polymer" or "cationic monomer" means not to contain a so-called "amphoteric" one having both of an atom having a positive charge and an atom having a negative charge.

In the present invention, the "amide group having only a nonionic substituent" is meant for one wherein an electrically neutral substituent is bonded directly to the nitrogen atom of an amide group, and in Examples in this specification, an amide group having a hydroxyethyl group bonded thereto, of HEAA, or an amide group having a methyl group bonded thereto, of DMAA used in copolymers (i), (ii) and (vii), corresponds thereto.

Further, in this specification, the "polymer" includes a polymer derived from a natural product. Further, "(meth) acrylate" is a general term for an acrylate and a metal acrylate. The same applies with respect to "(meth)acrylamide" and "(meth)acrylic acid."

Further, in this specification, the expression "to" is used to include the numerical values before and after "to" as the lower and higher limit values.

<Cosmetic Composition)

The cosmetic composition of the present invention means an optional cosmetic preparation to be used for the hair and skin, and it widely includes so-called cosmetic preparations, such as a shampoo, a rinse, a conditioner, a treatment, a hair coloring agent, a permanent wave agent, an out-bath treatment, a hair pack, a hair spray, a hair foam, a styling agent, a body shampoo, a make cleansing, a hand soap, a milky lotion, a skin lotion, a lotion, a cream, a beauty essence, a sunscreen, a foundation, a lip stick, a mascara, an eye shadow, a depilation agent, etc. Further, the manner of its use may include one wherein it is applied and well spread over the skin, hair, etc., followed by rinsing (washing off) and one not followed by rinsing.

The cosmetic composition of the present invention is particularly preferably used for the hair, and a hair wash made of the cosmetic composition of the present invention is preferred as it is excellent in the anti-dandruff effect. Here, the hair wash is one which is applied to the hair and then rinsed off, and it may, for example, be a shampoo, a rinse, a conditioner or a treatment. Improvement of the anti-dandruff effect is attributable to improvement of the amount of adsorption of a metal pyrithione salt to exhibit the anti-dandruff effect on the hair.

Usually, at the time of diluting a shampoo with water for the purpose of making the touch smooth at the time of rinsing the shampoo from the hair, it is necessary to design the composition of a polymer and a hair cosmetic so that a water-insoluble precipitate (hereinafter sometimes referred to as a complex) composed of a cationic polymer and a surfactant, will form.

As a method to let a metal pyrithione salt (particularly zinc pyrithione) as an anti-dandruff agent be substantially adsorbed on the hair, it is conceivable (1) to let the precipitate take in the metal pyrithione salt, or (2) to let the precipitate be substantially adsorbed on the hair during rinsing.

As a specific method for (1) (as a method for letting the precipitate take in a large amount of the metal pyrithione salt), it is effective to increase the interaction of a copolymer to a metal ion as a constituting component of the metal pyrithione salt and for example, it is considered preferred to obtain a large amount of e.g. a hydroxy group having a chelate effect, as a constituting unit of the copolymer.

Further, as a specific method for (2) (as a method for letting the precipitate be substantially adsorbed on the hair at the time of rinsing), it may, for example, be mentioned that the copolymer has a suitable amount of a cationic group or a structural flexibility, or the copolymer has a structure having a high affinity to the hair surface. For the precipitate to satisfy such conditions, it is conceivable, for example, to control the amount of a cationic group by the amount of constituting units of the polymer, to use an acrylic resin for the main chain of the copolymer to let the structure have flexibility, or to adopt a structure having a hydrogen-bonding property, such as an amide group, to increase the affinity to the hair.

In view of the foregoing, the first cosmetic composition of the invention is a cosmetic composition comprising a cationic polymer and a metal pyrithione salt, wherein the cationic polymer has a cationic group and at least one group selected from a hydroxy group and an amide group having only a nonionic substituent; the amount of the cationic group is from 0.1 to 10.0 meq/g; at least one of the amount of the hydroxy group being from 1.5 to 20.0 meq/g and the amount of the amide group having only a nonionic substituent being from 1.5 to 10.0 meq/g, is satisfied. And when the cosmetic composition is used as a hair wash, the amount of adsorption of the metal pyrithione salt is at least 20 µg/g on at least one of untreated hair and damaged hair.

Further, the second cosmetic composition of the invention is a cosmetic composition comprising a copolymer (1) and a metal pyrithione salt, wherein the copolymer contains constituting units corresponding to a cationic vinyl monomer (A) represented by the following formula (I) and constituting units corresponding to a nonionic vinyl monomer (B) represented by the following formula (II) and/or (III); the proportion of the constituting units corresponding to the cationic vinyl monomer (A) is from 10 to 80 wt % to the total constituting units constituting the copolymer; and the weight average molecular weight of the copolymer is from 10,000 to 2,000,000.

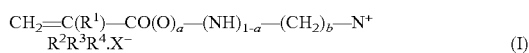

In the above formula (I), $R^1$ is a hydrogen atom or a methyl group, each of $R^2$ and $R^3$ which are independent of each other, is a $C_{1-24}$ alkyl group, a $C_{1-24}$ aryl group or a $C_{1-24}$ aralkyl group, $R^4$ is a hydrogen atom, a $C_{1-24}$ alkyl group, a $C_{1-24}$ aryl group, a $C_{1-24}$ aralkyl group or $-CH_2-CH(OH)-CH_2-N^+R^5R^6R^7.Y^-$, each of $R^5$ to $R^7$ which are independent of one another, is a $C_{1-24}$ alkyl group, a $C_{1-24}$ aryl group or a $C_{1-24}$ aralkyl group, each of $X^-$ and $Y^-$ which are independent of each other, is an anion, a is 0 or 1, and b is an integer of from 1 to 10. Further, in the formula (II), $R^8$ is a hydrogen atom or a methyl group, and X is a bivalent linking group containing at least two hydroxy groups. Further, in the formula (III), $R^9$ is a hydrogen atom or a methyl group, and each of $R^{10}$ and $R^{11}$ which are independent of each other, is a hydrogen atom, a $C_{1-4}$ alkyl group or a $C_{1-4}$ hydroxyalkyl group.

<Cationic Polymer>

The cationic polymer to be used for the cosmetic composition of the present invention is one having a cationic group, and the upper limit of the amount of the cationic group is usually 10.0 meq/g, preferably 5.0 meq/g, and the lower limit is usually 0.1 meq/g, preferably 0.4 meq/g. If the amount of the cationic group is larger than 10.0 meq/g, the formulation property tends to be deteriorated, such that when a shampoo is formulated, aggregates are likely to be formed, and if it is smaller than 0.1 meq/g, the adsorption property on the hair tends to be low when the composition is used as a hair wash.

The cationic polymer to be used for the cosmetic composition of the present invention is required to contain, in its structure, at least one functional group selected from a hydroxy group and an amide group having only a nonionic substituent. The upper limit of the amount of the hydroxy group is usually 20.0 meq/g, preferably 15.0 meq/g, particularly preferably 10.0 meq/g, and the lower limit is usually 1.5 meq/g, preferably 2.0 meq/g, particularly preferably 2.5 meq/g. Further, the upper limit of the amount of the amide group having only a nonionic substituent is usually 10.0 meq/g, preferably 8.0 meq/g, more preferably 6.0 meq/g, and the lower limit is usually 1.5 meq/g, preferably 2.0 meq/g, more preferably 2.5 meq/g.

The cationic polymer of the present invention is one which satisfies at least one of the above amount of the hydroxy group and the above amount of the amide group having only a nonionic substituent. However, in a case where the cationic polymer is one not containing an amide group having only a nonionic substituent, the amount of the hydroxy group is preferably at least 4.2 meq/g in order to increase the effect for adsorption of the metal pyrithione salt. If the amount of the hydroxy group is larger than 20.0 meq/g or if the amount of the amide group having only a nonionic substituent is larger than 10.0 meq/g, the hydrophilicity of the copolymer tends to be high, and precipitates tend to be hardly formed during rinsing. Further, if the amount of the hydroxy group is smaller than 1.5 meq/g, and the amount of the amide group having only a nonionic substituent is smaller than 1.5 meq/g, the amount of adsorption of the metal pyrithione salt tends to be small.

Thus, the polymer contained in the cosmetic composition of the present invention is one containing at least one of the hydroxy group and the amide group having only a nonionic substituent, wherein the amount of the hydroxy group is from 1.5 to 20.0 meq/g; the amount of the amide group having only a nonionic substituent is from 1.5 to 10.0 meq/g; and further, the amount of the cationic group is from 0.1 to 10.0 meq/g. In this specification, the amount of each functional group represents the mg equivalent of the functional group per 1 g of the cationic polymer and can be determined or analyzed by various methods. However, it is simple to regard it as the value of the charged amount at the time of preparation of the polymer, and also in Examples of this application, such a method is adopted.

The cationic polymer of the present invention is not particularly limited, so long as it satisfies the above-mentioned amounts of the respective functional groups, but specific examples may be a cation-modified cellulose ether derivative, a cation-modified galactomannan polysaccharide, a copolymer of a dimethyldiallylammonium halide with acrylamide, a copolymer of a diallyldimethylammonium chloride with vinyl pyrrolidone, a copolymer of a polymerizable vinyl monomer containing a quaternary ammonium group, with various vinyl monomer, etc.

Further, as the above-mentioned copolymer of a polymerizable vinyl monomer containing a quaternary ammonium group with various vinyl monomer, a particularly preferred example may be a combination of one or two among N-(meth)acryloyloxyethyl-N,N,N-trimethylammonium chloride and N-(meth)acryloylaminopropyl-N,N,N-trimethylammonium chloride, and at least one selected from the group consisting of N-hydroxyethylacrylamide, N,N-dimethylacrylamide, 2,3-dihydroxypropyl methacrylate and 2-hydroxyethyl methacrylate.

Further, as the cationic polymer of the present invention, it is also possible to use, other than those described above, one contained in the copolymer (1) as described below, so long as it satisfies the amounts of the respective functional groups. Further, the above-mentioned cationic polymers may, respectively, be used alone, or two or more of them may be used in combination.

<Copolymer (1)>

As the polymer to be used for the cosmetic composition of the present invention, a copolymer (hereinafter sometimes referred to as copolymer (1)) may be mentioned which contains constituting units corresponding to a cationic vinyl monomer (A) represented by the formula (I) and constituting units corresponding to a nonionic vinyl monomer (B) represented by the formula (II) or (III).

The copolymer (1) contained in the cosmetic composition of the present invention has a structure corresponding to a copolymer of a monomer mixture comprising a vinyl monomer having a cationic group and a nonionic vinyl monomer. That is, it is a copolymer containing constituting units corresponding to a cationic vinyl monomer (A) represented by the formula (I) (hereinafter sometimes referred to as the cationic vinyl monomer (A)) and constituting units corresponding to a nonionic vinyl monomer (B) represented by the formula (II) or (III) (hereinafter sometimes referred to as the nonionic vinyl monomer (B)).

The cationic vinyl monomer (A) is not particularly limited so long as it is a (meth)acrylic quaternary ammonium salt monomer represented by the following formula (I), and it may, for example, be a (meth)acrylic acid ester type quaternary ammonium salt such as N-methacryloyloxyethyl-N,N,N-trimethylammonium chloride, or a (meth)acrylamide type quaternary ammonium salt such as N-methacryloylaminopropyl-N,N,N-trimethylammonium chloride.

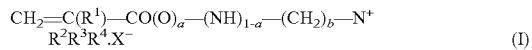

(wherein $R^1$ is a hydrogen atom or a methyl group, each of $R^2$ and $R^3$ which are independent of each other, is a $C_{1-24}$ alkyl group, a $C_{1-24}$ aryl group or a $C_{1-24}$ aralkyl group, $R^4$ is a hydrogen atom, a $C_{1-24}$ alkyl group, a $C_{1-24}$ aryl group, a $C_{1-24}$ aralkyl group or —CH$_2$—CH(OH)—CH$_2$—N$^+$R$^5$R$^6$R$^7$.Y$^-$, each of $R^5$ to $R^7$ which are independent of one another, is a $C_{1-24}$ alkyl group, a $C_{1-24}$ aryl group or a $C_{1-24}$ aralkyl group, each of X$^-$ and Y$^-$ which are independent of each other, is an anion, a is 0 or 1, and b is an integer of from 1 to 10.)

$R^1$ is preferably a methyl group, and each of $R^2$ and $R^3$ which are independent of each other, is preferably a $C_{1-24}$ alkyl group, more preferably a methyl group or an ethyl group, particularly preferably a methyl group. $R^4$ is preferably a $C_{1-24}$ alkyl group, more preferably a methyl group, an ethyl group or a butyl group, particularly preferably a methyl group. Each of $R^5$ to $R^7$ which are independent of one another, is preferably a $C_{1-24}$ alkyl group, more preferably a methyl group or an ethyl group, particularly preferably a methyl group. Each of anions represented by X$^-$ and Y$^-$ which are independent of each other, is preferably a chlorine ion, an iodine ion or a bromine ion. b is preferably an integer of from 1 to 5, more preferably 2 or 3.

Some of the cationic vinyl monomer (A) may be exemplified as follows: a (meth)acrylic acid ester having a cationic group, such as N-(meth)acryloyloxyethyl-N,N,N-trimethylammonium chloride, N-(meth)acryloyloxyethyl-N-ethyl-N,N-dimethylammonium=monoethyl sulfate, N-(meth)acryloyloxyethyl-N,N,N-triethylammonium=monoethyl sulfate, N-[3-{N'-(meth)acryloyloxyethyl-N',N'-dimethylammonium}-2-hydroxypropyl]-N,N,N-trimethylammonium chloride or N-[3-{N'-(meth)acryloyloxyethyl-N',N'-diethylammonium}-2-hydroxypropyl]-N,N,N-triethylammonium chloride; a (meth)acrylamide having a cationic group, such as N-(meth)acryloylaminopropyl-N,N,N-trimethylammonium chloride, N-(meth)acryloylaminopropyl-N-ethyl-N,N-dimethylammonium=monoethyl sulfate, N-(meth)acryloylaminopropyl-N,N-diethyl-N-methylammonium chloride, N-(meth)acryloylaminopropyl-N,N-diethyl-N-methylammonium=monomethyl sulfate, N-[3-{N'-(meth)acryloylaminopropyl-N',N'-dimethylammonium}-2-hydroxypropyl]-N,N,N-trimethylammonium chloride or N-[3-{N'-(meth)acryloylaminopropyl-N',N'-diethylammonium}-2-hydroxypropyl]-N,N,N-trimethylammonium chloride; etc.

Among them, N-(meth)acryloyloxyethyl-N,N,N-trimethylammonium chloride or N-(meth)acryloylaminopropyl-N,N,N-trimethylammonium chloride is preferably employed, and particularly preferred is N-(meth)acryloylaminopropyl-N,N,N-trimethylammonium chloride.

Further, the constituting units corresponding to the cationic vinyl monomer (A) of the copolymer (1) may be obtained, for example, by polymerizing the above-described cationic vinyl monomer (A), or may otherwise be obtained by copolymerizing a precursor of a cationic vinyl monomer represented by the following formula (IV), followed by a cationization reaction by means of a cationization agent to cationize the copolymer to convert it to a structure having the corresponding cationic group.

(wherein $R^1$ to $R^3$, a and b are as defined above in the above formula (I), and the preferred ranges are also the same.)

The precursor of the cationic vinyl monomer may, for example, be a (meth)acrylic acid ester having a tertiary amine structure, such as N-(meth)acryloyloxyethyl-N,N-dimethylamine or N-(meth)acryloyloxyethyl-N,N-diethylamine; or a (meth)acrylamide having a tertiary amine structure, such as N-(meth)acryloylaminopropyl-N,N-dimethylamine or N-(meth)acryloylaminopropyl-N,N-diethylamine.

The cationization agent may, for example, be an alkyl halide such as methyl chloride, or a cation group-containing cationization agent such as 3-chloro-2-hydroxypropyl-N,N,N-trimethylammonium chloride. The cationization reaction may be carried out, for example, by adding the cationization agent to a solution of the copolymer under a condition of from 20 to 100° C. for from 1 to 20 hours.

Further, as such a cationic vinyl monomer (A) or its precursor, one type may be used alone or two or more types may be used in combination.

In the copolymer (1), the content of the constituting units corresponding to the cationic vinyl monomer (A) is preferably at least 10 wt %, more preferably at least 20 wt %, further preferably at least 25 wt % and preferably at most 80 wt %, more preferably at most 70 wt %, further preferably at most 60 wt %. Such constituting units corresponding to the cationic vinyl monomer (A) are considered to form, when an anionic surfactant is used in combination in the cosmetic composition, a complex therewith thereby to let the copolymer (1) readily deposit on the hair. By adjusting the constituting units corresponding to the cationic vinyl monomer (A) to be at least 10 wt %, it is possible to form a more sufficient complex with the anion surfactant and sufficiently maintain the strength of adsorption to the hair or the like, and by adjusting them to be at most 80 wt %, it is possible to formulate a cosmetic composition without bringing about aggregation, such being desirable.

The nonionic vinyl monomer (B) is not particularly limited so long as it is one represented by the following formula (II) or (III), and it is effective to impart hydrophilicity to the copolymer (1) due to the hydrophilicity derived from the nonionic vinyl monomer (B). It is considered that the solubility of the copolymer (1) in water is thereby improved, and also at the time when the copolymer (1) forms a complex with the surfactant, the solubility of the copolymer in water can be maintained. As the nonionic vinyl monomer (B), it is preferred to use two or more types of either one of the following formulae (II) and (III) in combination, and it is particularly preferred to use ones of the formulae (II) and (III) in combination.

(wherein $R^8$ is a hydrogen atom or a methyl group, and X is a bivalent linking group containing at least two hydroxy groups)

(wherein $R^9$ is a hydrogen atom or a methyl group, and each of $R^{19}$ and $R^{11}$ which are independent of each other, is a hydrogen atom, a $C_{1-4}$ alkyl group or a $C_{1-4}$ hydroxyalkyl group).

The nonionic vinyl monomer represented by the formula (II) is not particularly limited, so long as it is one included in this formula. However, it is preferred that X is a bivalent linking group which is a linking group having from 2 to 9 carbon atoms and containing at least two hydroxy groups, which may contain an oxygen atom and/or a nitrogen atom. More preferably, X is a bivalent linking group containing at least two hydroxy groups, which is represented by $\{-(CH_2)_c-(CR^{12}R^{13})_d-(CHOH)_e-(CH_2O)_f-\}$, wherein each of $R^{12}$ and $R^{13}$ which are independent of each other, is a $C_{1-3}$ alkyl group or a $C_{1-3}$ hydroxyalkyl group, c is an integer of from 1 to 4, d is 0 or 1, e is an integer of from 1 to 6, and f is an integer of from 0 to 2. Here, the order of four types of linking groups i.e. $-(CH_2)-$, $-(CR^{12}R^{13})-$, $-(CHOH)-$ and $-(CH_2O)-$ in $\{\ \}$ is optional, and they may be present at random. For example, in a case where c is 2, d 0, e 1 and f 0, the structure in $\{\ \}$ may be $\{-(CH_2)-(CH_2)-(CHOH)-\}$ or $\{-(CH_2)-(CHOH)-(CH_2)-\}$. Particularly preferably, X is a bivalent linking group containing at least two hydroxy groups, which is represented by $\{-(CH_2)_c-(CHOH)_e-\}$, $\{-(CH_2)_c-(CR^{12}R^{13})-(CHOH)-\}$ or $\{-[(CH_2)-(CHOH)-(CH_2O)]_g-\}$, wherein $R^{12}$, $R^{13}$ and c to f are as defined above, and g is an integer of from 1 to 3.

The nonionic vinyl monomer represented by the formula (II) may, for example, be 2,3-dihydroxypropyl (meth)acrylate, 2,3,4-trihydroxybutyl (meth)acrylate, 2,3,4,5,6-pentahydroxyhexyl (meth)acrylate, pentaerythritol (meth)acrylate, diglycerin (meth)acrylate or triglycerin (meth)acrylate. However, it is most preferably 2,3-dihydroxypropyl (meth)acrylate.

In the nonionic vinyl monomer represented by the formula (III), $R^9$ is preferably a hydrogen atom. Each of $R^{10}$ and $R^{11}$ which are independent of each other, is preferably a hydrogen atom, a $C_{1-4}$ alkyl group or a $C_{1-4}$ hydroxyalkyl group. The $C_{1-4}$ alkyl group or the $C_{1-4}$ hydroxyalkyl group may, for example, be a methyl group, an ethyl group, a propyl group, an isopropyl group, a butyl group, an isobutyl group, a hydroxymethyl group or a 2-hydroxyethyl group. The sum of the numbers of carbon atoms in $R^{10}$ and $R^{11}$ is preferably from 2 to 4, most preferably 2. a is preferably an integer of from 1 to 3, most preferably 2.

The nonionic vinyl monomer represented by the formula (III) is not particularly limited so long as it is included in this formula, and it may, for example, be an alkylacrylamide such as N-methyl (meth)acrylamide, N-ethyl (meth)acrylamide, N-propyl (meth)acrylamide or N-isopropyl (meth)acrylamide; a dialkylacrylamide such as N,N-dimethyl (meth)acrylamide or N,N-diethyl (meth)acrylamide; or a hydroxyalkyl (meth)acrylamide such as N-hydroxymethyl (meth)acrylamide, N-(2-hydroxyethyl) (meth)acrylamide, N,N-bis(hydroxymethyl) (meth)acrylamide or N,N-bis(2-hydroxyethyl) (meth)acrylamide.

One of such nonionic vinyl monomers (B) may be used alone, or two or more of them may be used in combination. It is preferred to employ the nonionic vinyl monomer represented by the formula (II), since the metal pyrithione salt persistence in the cosmetic composition is further improved.

The content of the structural units corresponding to the nonionic vinyl monomer (B) in the copolymer is preferably at least 20 wt %, more preferably at least 30 wt %, further preferably at least 40 wt % and preferably at most 90 wt %, more preferably at most 80 wt %, further preferably at most 75 wt %. By adjusting the structural units corresponding to the nonionic vinyl monomer (B) to be at least 20 wt %, the solubility of the copolymer (1) in water becomes high, and it becomes possible to maintain sufficient solubility in water even when, for example, it forms a complex with an anionic surfactant. Further, it is preferred to adjust them to be at most 90 wt %, so as to maintain the complex with the anionic surfactant.

In the copolymer (1), structural units derived from another vinyl monomer may further be contained. However, if an anionic functional group is present in the copolymer (1), such may hinder the formation of the complex especially when an anionic surfactant is employed, and accordingly, one containing little anionic functional group is preferred (for example, at most 10% in all functional groups), and one not substantially containing it, is more preferred. Here, not substantially containing is meant for one showing no anionic property e.g. at a pH of from 3 to 8.

Such another vinyl monomer may, for example, be a nonionic monomer such as an ester of a $C_{1-22}$ alcohol with (meth)acrylic acid, an amide of a $C_{1-22}$ alkylamine with (meth)acrylic acid, a monoester of ethylene glycol or 1,3-propylene glycol with (meth)acrylic acid, an ester having a hydroxy group of such a monoester etherified with e.g. methanol or ethanol, (meth)acryloylmorpholine, hydroxymethylacrylamide, or hydroxyethylacrylamide; an amino acid-type cationic monomer such as a diallyl type quaternary ammonium salt such as N,N-dimethyl-N,N-diallylammonium chloride, or a reaction product of L-arginine with glycidyl methacrylate; an amphoteric monomer such as a betaine group-containing (meth)acrylester, or a betaine group-containing (meth)acrylamide; or a semipolar monomer such as an amineoxide group-containing (meth)acrylester, or an amineoxide group-containing (meth)acrylamide.

The content of the structural units derived from another vinyl monomer in the copolymer (1) may suitably be determined within a range not to depart from the concept of the present invention. For example, it may be suitably determined within a range not to impair the solubility as the water-soluble resin or not to impair the conditioning effect in a case where it is used for a cosmetic composition for the hair. Usually, it is preferably at most 30 wt %, more preferably at most 20 wt %, in the copolymer (1).

The contents of the constituting units corresponding to the cationic vinyl monomer (A), constituting units corresponding to the nonionic vinyl monomer (B) and the constituting units derived from another vinyl monomer, in the copolymer (1), can be obtained from the amounts of the respective monomers used. However, they can also be obtained by measuring IR absorption of a hydroxy group or an amide bond moiety, $^1$H-NMR of a hydroxy group or an amide bond moiety, or a methyl group adjacent to a cation group, or $^{13}$C-NMR thereof.

The copolymer (1) to be used in the present invention preferably has a solubility in water to such an extent that it is capable of forming an aqueous solution having a concentration of at least 5 wt % at room temperature i.e. at 25° C. That is, it is preferably a water-soluble resin such that its aqueous solution at a concentration of at least 5 wt % has a transmittance to water at a wavelength of 550 nm being at least 80%, and the aqueous solution is uniform and stable. More preferred is one capable of forming an aqueous solution having a concentration of at least 20 wt %.

The copolymer (1) of the present invention can be produced, for example, by mixing monomers to present the respective constituting units, or their precursors, and copolymerizing them by a method such as solution polymerization, suspension polymerization or emulsion polymerization, followed by cationization reaction as the case requires.

The polymerization reaction is preferably carried out in water and/or a hydrophilic solvent. The hydrophilic solvent may, for example, be a ketone solvent such as acetone, methyl ethyl ketone or methyl isobutyl ketone; or an alcohol solvent such as methanol, ethanol, n-propanol, i-propanol, n-butanol, i-butanol or sec-butanol. Such water and/or a hydrophilic solvent may be used alone, or two or more of them may be used in combination. It is particularly preferred to employ an alcohol solvent or water.

For the polymerization reaction, a polymerization initiator may be used. As the polymerization initiator, an azo compound such as 2,2'-azobisisobutyronitrile, 2,2'-azobis(2-methyl-N-(2-hydroxyethyl)-propionamide), 2,2'-azobis(2,4-dimethylvaleronitrile), 2,2'-azobis(4-methoxy-2,4-dimethylvaleronitrile), dimethyl-2,2'-azobisisobutyrate, 2,2'-azobis(2-methylbutyronitrile), 1,1'-azobis(1-cyclohexanecarbonitrile), 2,2'-azobis(2-methyl-N-(2-hydroxyethyl)-propionamide) or 2,2'-azobis(2-amidinopropane)dihydrochloride, a peroxide such as benzoyl peroxide, dicumyl peroxide, di-t-butyl peroxide or lauroyl peroxide, a persulfate, or its redox may, for example, be used without any particular restriction. The polymerization initiator is used preferably within a range of from 0.01 to 5 wt %, more preferably within a range of from 0.1 to 3 wt %, based on all monomers.

The polymerization reaction can be carried out, for example, in an inert gas atmosphere such as nitrogen or argon, preferably at a temperature of from 30 to 120° C., more preferably from 40 to 100° C., usually for from 1 to 30 hours. After completion of the polymerization, the formed copolymer is preferably isolated from the reaction solution by a suitable means such as distillation of the solvent or addition of a poor solvent. The obtained copolymer (1) may be used as it is or after purifying it, for the preparation of the cosmetic composition of the present invention. The purification may be carried out by suitable means such as reprecipitation, washing with a solvent, membrane separation, etc. in combination, as the case requires.

As the copolymer (1) to be used in the present invention, it is possible to utilize one having an optional structure such as a random copolymer, a block copolymer or a graft copolymer, without any particular restriction.

The random copolymer can be prepared, for example, by a method of adding an initiator to a mixture of all monomers to be used for the polymerization thereby to react them all at once, or a method of gradually reacting them while dropwise adding a part or all amount of the monomers. It is also possible to carry out the polymerization by dropwise adding the monomers while changing the monomer composition. The block copolymer can be prepared by utilizing e.g. a known radical initiator or catalyst. The graft copolymer can be prepared by a method of utilizing a macromer having a vinyl functional group or a method of reacting polymers having reactive functional groups to each other.

Among them, one which can be prepared from an inexpensive raw material without requiring a special step, is preferred with a high industrial applicability, and a random copolymer is most preferred which can be most easily prepared by using a usual raw material.

Further, at the time of formulating the copolymer (1) into a cosmetic composition, a plurality of copolymers may be used in combination. In such a case, copolymers may be separately prepared and then mixed and formulated. Otherwise, one copolymer is firstly prepared, and in the reaction liquid, a monomer component to constitute another copolymer is added and polymerized to obtain a mixture of two copolymers. Likewise, by repeating addition and polymerization of a monomer component, it is possible to obtain a mixture of more copolymers. In the present invention, the latter method is preferred whereby the mixture can be simply prepared.

The weight average molecular weight of the copolymer (1) is preferably from 10,000 to 2,000,000. By adjusting the weight average molecular weight to be at least 10,000, it is possible to improve the metal pyrithione salt delivery effect especially at the time of using an anion surfactant, by deposition of a complex formed with the anion surfactant on the hair or skin. The weight average molecular weight is more preferably at least 100,000, further preferably at least 200,000. By adjusting it to be at most 2,000,000, it is possible to maintain the viscosity of the copolymer (1) solution to be proper, whereby the formulation property is improved, and the handling efficiency for the production will be facilitated. The weight average molecular weight of the copolymer (1) can be measured by gel permeation chromatography (using e.g. water/methanol/acetic acid/sodium acetate as a developing solvent) and can be determined by using polyethylene glycol as a standard substance. It is more preferably at most 1,000,000, further preferably at most 700,000.

The viscosity of the copolymer (1) solution is preferably within a proper range, for example, at a level where a 20 wt % aqueous solution of the copolymer (1) can be prepared. The viscosity of the 20 wt % aqueous solution at 25° C. is more preferably at most 100,000 mPa·s, further preferably at most 50,000 mPa·s, still further preferably at most 20,000 mPa·s, most preferably at most 5,000 mPa·s. However, it is usually at least 10 mPa·s. That is, at a high concentration, transportation as a product is facilitated.

The viscosity can be adjusted by controlling the polymerization degree of the copolymer (1). Further, the molecular weight and viscosity can be controlled also by adding a crosslinking agent such as a polyfunctional acrylate or by increasing or decreasing the amount of its addition. However, if the crosslinking agent is added excessively even to a small extent, it may become difficult to control the molecular weight and viscosity for the industrial production, as the molecular weight and viscosity are likely to abruptly increase. If the molecular weight and viscosity become too high, the formulation property will be deteriorated as mentioned above, such being undesirable. Therefore, the amount of the crosslinking agent to be used is preferably controlled to be an amount within a range where the molecular weight will not increase at the time of the polymerization. For example, it is at most 0.1 wt %, more preferably at most 0.01 wt %, to the amount of the copolymer (1). Most preferably, a crosslinking agent is not used at the time of the polymerization of the copolymer (1), and no crosslinking agent is contained as a constituting component of the copolymer (1).

As a method for controlling the molecular weight of a copolymer (1), a method of using a chain transfer agent at the time of the polymerization may be mentioned. By an addition of a chain transfer agent, it is possible to lower the molecular weight. However, there may be a case where control becomes difficult in an industrial production, such that if the added amount is too much, the molecular weight tends to be too low. Further, a thiol which is commonly used as a chain transfer agent, such as thioglycol, an alkylthiol or thioglycolic acid, has such a demerit that it causes deterioration of the odor. Accordingly, it is preferred not to contain a chain transfer agent.

The content of the copolymer (1) in the cosmetic composition of the present invention is not particularly limited, and a suitable amount may be used depending upon its application. Particularly in the case of a hair-wash, the content is preferably from 0.05 to 2 wt %, more preferably at least 0.1 wt %, further preferably at least 0.2 wt %, in the composition.

<Metal Pyrithione Salt>

The cosmetic composition of the present invention further contains a metal pyrithione salt in addition to the polymer of the present invention. The metal pyrithione salt has an antibacterial effect, and when it is incorporated to a cosmetic composition, it exhibits an anti-dandruff effect. By using e.g. a hair wash having the metal pyrithione salt incorporated, it is permitted to stay on the hair to exhibit such an effect, and the more the residual amount, the higher the anti-dandruff effect. In the cosmetic composition of the present invention, the metal pyrithione salt is blended with the polymer of the present invention, whereby it is possible to realize an excellent metal pyrithione salt persistence on the hair, skin, etc. after the use of the cosmetic composition.

In the first embodiment of the present invention, when the cosmetic composition of the present invention is used as a hair wash, the amount of adsorption of the metal pyrithione salt is usually at least 20 μg/g on at least one of untreated hair and damaged hair. And, depending upon the type of the polymer (or the types and combination of monomers as raw materials for the polymer), the combination, etc. constituting the cosmetic composition, the amount of adsorption is preferably at least 30 μg/g, more preferably at least 40 μg/g, further preferably at least 65 μg/g.

Further, the present invention places more emphasis on the metal pyrithione salt adsorption effect on untreated hair than on damaged hair. Accordingly, upon satisfying the amount of adsorption of the metal pyrithione salt being at least 65 μg/g on at least one of untreated hair and damaged hair, the amount of adsorption on untreated hair is more preferably at least 65 μg/g, particularly preferably at least 180 μg/g, most preferably at least 295 μg/g. Further, the amount of adsorption of the metal pyrithione salt which can be accomplished by the construction of the present invention is at a level of 2,000 μg/g on each of untreated hair and damaged hair.

Here, the reason as to why emphasis is placed particularly on the amount of adsorption of the metal pyrithione salt on untreated hair in the present invention, is as follows. The anti-dandruff agent represented by the metal pyrithione salt, particularly zinc pyrithione, is one exhibiting the effect by killing bacteria. Accordingly, it is preferred that the anti-dandruff agent is adsorbed in a substantial amount at the portion close to the scalp. In general, the hair at the portion close to the scalp is healthy hair, and the hair at the portion remote from the scalp is one physically damaged by e.g. heat or ultraviolet ray. With respect to untreated hair and damaged hair in the present invention, untreated hair rather than damaged hair is in a healthy hair state close to the scalp, and therefore, the amount of adsorption of the metal pyrithione salt on untreated hair is emphasized than on damaged hair. Here, the method for evaluating the amount of adsorption of the metal pyrithione salt on untreated hair and damaged hair is as follows.

(Evaluation Method)

A hair wash is applied to a prepared hair bundle, and then, the amount of adsorption of the metal pyrithione salt on the hair is quantitatively determined. The hair bundle to be used is as "untreated hair" "human black hair (100%) bundled at the root (untreated hair: 10 g×30 cm); manufactured by Beaulax". Further, as "damaged hair", one having the "untreated hair" subjected to bleach treatment is used. Here, bleach treatment is carried out in such a manner that as the bleaching agent, a mixture comprising 12 g of Promatiz Flaeve oxytan 6.0 (6% hydrogen peroxide cream) manufactured by Milbon Co., Ltd. and 26 g of Powder Bleach MR manufactured by Meros Chemical Company, is applied to one hair bundle and left to stand for 30 minutes, followed by washing with water, and further, polyoxyethylene (3) lauroyl ether sodium sulfate is applied, followed by washing.

(Amount of Adsorption of Metal Pyrithione Salt)

About 10 g of the hair bundle is wet with running water of 40° C. for 30 seconds and then drained off until water droplets will no longer drop, whereupon 1 g of the hair wash is applied and bubbled by running a comb through the hair 100 times per minute. The hair bundle is rinsed with running water at 40° C. for 30 seconds and then dried overnight at a temperature of 23° C. under a humidity of 60%. Thereafter, the hair bundle is immersed for two minutes in a 0.5N potassium hydroxide methanol/water (4/1 (weight ratio)) solution to extract zinc pyrithione adsorbed on the hair thereby to obtain an extract solution. The amount of adsorption of the metal pyrithione salt is evaluated by the absorbance determination (288 nm) of the extract solution. A calibration curve is preliminarily prepared by a plurality of standard samples having different concentrations by dissolving the metal pyrithione salt in a 0.5N potassium hydroxide (KOH) methanol/water (4/1 (weight ratio)) solution, and the amount of adsorption is determined from the measured absorbance of the extract solution and the calibration curve. Here, a blank in the absorbance determination is an extracted solution obtained by immersing "untreated hair" in a 0.5N KOH methanol/water (4/1 (weight ratio)) solution for two minutes. Further, the amount of adsorption of the metal pyrithione salt is calculated as the amount of adsorption of the metal pyrithione salt per unit weight of the hair by preliminarily measuring the weight of each hair bundle.

In a case where the cosmetic composition of the present invention is used as a hair wash, a high adsorption of the metal pyrithione salt on the hair is shown, because the copolymer has a cationic group amount and an amide group amount capable of precipitating a precipitate having a high persistence on the hair, or the copolymer contains a structure to increase the mutual action between the precipitate and the metal pyrithione salt.

The reason for the improvement of the metal pyrithione salt persistence by the combined use of the polymer of the present invention and the metal pyrithione salt, is not clearly understood, but it is considered that the polymer of the present invention improves the dispersibility of the metal pyrithione salt, and when an anion surfactant is used, the cationic polymer or the copolymer (1) will form a complex with e.g. the anion surfactant, which will also act on the metal pyrithione salt at the time of deposition on the hair or skin thereby to provide an effect to promote deposition of the metal pyrithione salt on the hair or skin or to prevent it from being washed off, whereby the metal pyrithione salt persistence will be improved.

The metal pyrithione salt is not particularly limited, but it is preferably a pyrithione salt of zinc, tin, cadmium, magnesium, aluminum or zirconium. Among them, zinc pyrithione (zinc bis-[1-hydroxy-2(1H)-pyridinethionate]) as a pyrithione salt of zinc is particularly preferred.

The blend proportion of the metal pyrithione salt in the cosmetic composition of the present invention varies depending upon the function to be imparted to the composition, but, it may, for example, be preferably from 0.05 to 2 wt %, based on the entire composition.

<Anion Surfactant>

Further, it is preferred to further incorporate an anion surfactant to the cosmetic composition of the present invention in order to more effectively utilize the residual effect of the metal pyrithione salt in the cosmetic composition.

The amount of the anion surfactant to be used is usually from 1 to 25 wt %, preferably from 5 to 20 wt %. If the amount is less than 1 wt %, the washing function may be impaired when used as a washing liquid. On the other hand, if it exceeds 25 wt %, the viscosity of the washing liquid may be hardly increased, or formation of the precipitate may be impaired.

As such an anion surfactant, one commonly used in a washing liquid composition, may be used such as an α-olefin sulfonate, a higher alcohol sulfuric acid ester salt, a polyoxyethylene alkyl ether sulfuric acid ester salt, a paraffin sulfonate, a polyoxyethylene alkyl ether carboxylate, an alkylsulfosuccinate, an N-acyl-β-alanine salt, an N-acyl glutamate or an acyl methyl taurine salt. A counter ion of such an anion surfactant may, for example, be sodium, potassium, ammonium, triethanolamine or diethanolamine. Further, a plurality of anion surfactants may be used in combination.

<Optional Components>

To the cosmetic composition of the present invention, in addition to the above components, components capable of being commonly blended to cosmetics may optionally be incorporated. Such other components to be incorporated to the cosmetic composition are not particularly limited and may be blended within a range not to impair the object or effects of the present invention. As such components, the following may be mentioned, and in addition to the cationic polymer or the copolymer (1), and the metal pyrithione salt, the following components may suitably be blended to prepare the cosmetic composition of the present invention.

A water-soluble polymer may, for example, be methylcellulose or hydroxymethylcellulose. Further, an anionic polymer may, for example, be an acrylic acid derivative (such as a polyacrylic acid or its salt, or an acrylic acid/acrylamide/ethyl acrylate copolymer or its salt), a methacrylic acid derivative or a crotonic-acid derivative; a nonionic polymer may, for example, be an acrylic acid derivative (such as a hydroxyethyl acrylate/methoxyethyl acrylate copolymer or a polyacrylamide), or a vinyl pyrrolidone derivative (such as a polyvinylpyrrolidone or a vinylpyrrolidone/vinyl acetate copolymer); and an amphoteric polymer may, for example, be dimethyldiallylammonium chloride derivative (such as an acrylamide/acrylic acid/dimethyldiallylammonium chloride copolymer, or an acrylic acid/dimethyldiallylammonium chloride copolymer). These additional components may preferably be contained in an amount of from 0.1 to 1 wt % in the cosmetic composition.

The amphoteric surfactant may, for example, be an imidazoline type amphoteric surfactant such as sodium 2-undecyl-N,N,N-(hydroxyethylcarboxymethyl)-2-imidazoline, or 2-cocoyl-2-imidazolinium hydroxide-1-carboxyethyloxy disodium salt; or a betaine type surfactant such as 2-heptadecyl-N-carboxymethyl-N-hydroxyethyl imidazolinium betaine, lauryldimethylamino succinic acid betaine, an alkylbetaine, an amidebetaine or a sulfobetaine.

A hydrophilic nonionic surfactant may, for example, be a polyoxyethylene (hereinafter sometimes referred to as POE) sorbitan fatty acid ester (such as POE sorbitan monooleate, POE sorbitan monostearate, POE sorbitan monooleate or POE sorbitan tetraoleate); a POE sorbitol fatty acid ester (such as POE sorbitol monolaurate, POE sorbitol monooleate, POE sorbitol pentaoleate or POE sorbitol monostearate); POE glycerol fatty acid ester (such as POE monooleate such as POE glycerol monostearate, POE glycerol monoisostearate or POE glycerin triisostearate); a POE fatty acid ester (such as POE distearate, POE monodioleate, or ethylene glycol distearate); a POE alkyl ether (such as POE lauryl ether, POE oleyl ether, POE stearyl ether, POE-behenyl ether, POE-2-octyldodecyl ether or POE cholestanol ether); a Pluronic type (such as Pluronic); a POE.polyoxypropylene (hereinafter sometimes referred to as POP) alkyl ether (such as POE.POP cetyl ether, POE.POP-2-decyltetradecyl ether, POE.POP monobutyl ether, POE.POP hydrogenated lanolin or POE.POP glycerol ether); a tetra POE.tetra POP ethylenediamine condensate (such as tetronic); a POE caster oil-hardened caster oil derivative (such as POE caster oil, POE hardened caster oil, POE hardened caster oil monoisostearate, POE hardened caster oil triisostearate, POE hardened caster oil monopiroglutamic acid monoisostearic acid diester, or POE hardened caster oil maleic acid); a POE bee's wax•lanolin derivative (such as POE sorbitol bee's wax); an alkanol amide (such as coconut oil fatty acid diethanolamide, lauric acid monoethanolamide, or fatty acid isopropanolamide); a POE propylene glycol fatty acid ester; a POE alkylamine; a POE fatty acid amide; sucrose fatty acid ester; an alkylethoxydimethylamineoxide; or a trioleyl phosphoric acid.

A lipophilic nonionic surfactant may, for example, be a sorbitan fatty acid ester (such as sorbitan monooleate, sorbitan monoisostearate, sorbitan monolaurate, sorbitan monopalmitate, sorbitan monostearate, sorbitan sesquioleate, sorbitan trioleate, penta-2-ethylhexylic acid diglycerol sorbitan, or tetra-2-ethylhexylic acid diglycerol sorbitan); glycerol polyglycerol fatty acid (such as mono cotton oil fatty acid glycerol, glycerol monoerucate, glycerol sesquioleate, glycerol monostearate, glycerol α,α'-oleic acid piroglutamate, or glycerol monostearate malic acid); a propylene glycol fatty acid ester (such as propylene glycol monostearate); a hardened caster oil derivative; or a glycerol alkyl ether.

An oil may, for example, be a chain polysiloxane (such as dimethylpolysiloxane, methylphenylpolysiloxane or diphenylpolysiloxane), a cyclic polysiloxane (such as octamethylcyclotetrasiloxane, decamethylcyclopentasiloxane or dodecamethylcyclohexasiloxane), a silicone resin having a three dimensional network structure, a silicone rubber, various modified silicone (such as an alkyl-modified silicone, a phenyl-modified silicone, an amino-modified silicone, a polyether-modified silicone, a fluorine-modified silicone), a straight chain alcohol (such as lauryl alcohol, cetyl alcohol, stearyl alcohol, behenyl alcohol, myristyl alcohol, oleyl alcohol, or setostearyl alcohol), a branched chain alcohol (such as monostearylglycerol ether (batyl alcohol), 2-decyltetradecinol, lanolin alcohol, cholesterol, phytosterol, hexyldodecanol, isostearyl alcohol or octyldodecanol), olive oil, jojoba oil, liquid paraffin, or a fatty acid alkyl ester oil. The oil is preferably contained in an amount of from 0.1 to 3 wt % in the cosmetic composition.

Antibacterial active substances other than the metal pyrithione salt having an anti-dandruff effect may, for example, be piroctoneolamine (1-hydroxy-4-methyl-6-(2,4,4-trimethylpentyl)-2(1H)-pyrrolidone monoethanolamine), cyclopyrroxolamine (6-cyclohexyl-1-hydroxy-4-methyl-2(1H)-pyrrolidone monoethanolamine), selenium sulfide, particulate sulfur, coal tar, sulfur, whitfield ointment, castellani embrocation, aluminum chloride, gentian violet, undecylenic acid or its metal salt, potassium permanganate, sodium thiosulfate, propylene glycol, bitter orange oil, urea preparation, griseofulvin, 8-hydroxyquinolin ciloquinol, thiobendazole, thiocarbamate, haloprogin, polyene, hydroxypyridone, morpholine, benzylamine, allylamine (such as terbinafine), tea tree oil, clove leaf oil, coriander, palmarosa, berberine, thyme red, oil of cinnamon, cinnamic aldehyde, citronellic acid, hinokitol, Ichithyol, Sensiva SC-50, Elestab HP-100, azelaic acid, lyticase, iodopropylbutyl carbamate (IPBC), isothiazalinone such as octylisothiazalinone and azole, and combinations thereof.

As other components, a natural extract from animals and plants or its derivatives, an organic acid such as citric acid or lactic acid, an inorganic salt such as sodium chloride, an amino acid (such as glutamic acid or its salts, arginine or its salts or glycine), a solubilizing agent (such as ethanol, isopropanol or butanol), a polyhydric alcohol (such as ethylene glycol, polyethylene glycol, propylene glycol, dipropylene glycol, polypropylene glycol, 1,3-butylene glycol, glycerol, diglycerol or isoprene glycol), sugar (such as sorbitol, maltitol, xylitol, glucose, fructose, mannitol or inositol), a high molecular weight substance such as hyaluronic acid, an antioxidant, an ultraviolet absorber, a fungicide, an antiseptic, a chelating agent, a flagrance, a coloring agent, a higher fatty acid, a thickener, a metal-sealing agent (such as an edetate), a pH-controlling agent, a foaming promoter, etc. may suitably be incorporated within a range not to impair the effects of the present invention.

EXAMPLES

Now, specific embodiments of the present invention will be described in further detail with reference to Examples and Comparative Examples, but it should be understood that the present invention is by no means restricted by such Examples.
<Evaluation Method>

A hair wash was applied to a prepared hair bundle, and then, the amount of adsorption of the zinc pyrithione on the hair was quantitatively determined. The hair bundle to be used was as "untreated hair" "human black hair (100%) bundled at the root (untreated hair: 10 g×30 cm); manufactured by Beaulax". Further, as "damaged hair", one having the "untreated hair" subjected to bleach treatment was used. Here, bleach treatment was carried out in such a manner that as the bleaching agent, a mixture comprising 12 g of Promatiz Flaeve oxytan 6.0 (6% hydrogen peroxide cream) manufactured by Milbon Co., Ltd. and 26 g of Powder Bleach MR manufactured by Meros Chemical Company, was applied to one hair bundle and left to stand for 30 minutes, followed by washing with water, and further, polyoxyethylene (3) lauroyl ether sodium sulfate was applied, followed by washing.
<Amount of Adsorption of Zinc Pyrithione>

About 10 g of the hair bundle was wet with running water of 40° C. for 30 seconds and then drained off until water droplets would no longer drop, whereupon 1 g of the hair wash was applied and bubbled by running a comb through the hair 100 times per minute. The hair bundle was rinsed with running water at 40° C. for 30 seconds and then dried overnight at a temperature of 23° C. under a humidity of 60%. Thereafter, the hair bundle was immersed for two minutes in a 0.5N potassium hydroxide methanol/water (4/1 (weight ratio)) solution to extract zinc pyrithione adsorbed on the hair thereby to obtain an extract solution. The amount of adsorption of the zinc pyrithione was evaluated by the absorbance determination (288 nm) of the extract solution. A calibration curve was preliminarily prepared by a plurality of standard samples having different concentrations by dissolving the zinc pyrithione in a 0.5N potassium hydroxide (KOH) methanol/water (4/1 (weight ratio)) solution, and the amount of adsorption was determined from the measured absorbance of the extract solution and the calibration curve. Here, a blank in the absorbance determination was an extracted solution obtained by immersing "untreated hair" in a 0.5N KOH methanol/water (4/1 (weight ratio)) solution for two minutes.

Further, the amount of adsorption of the zinc pyrithione was calculated as the amount of adsorption of the zinc pyrithione per unit weight of the hair by preliminarily measuring the weight of each hair bundle.

<Measurement of Weight Average Molecular Weight>

The weight average molecular weight of a copolymer (i) was measured by means of gel permeation chromatography (apparatus: manufactured by Tosoh Corporation, SC8010, SD8022, RI8020, CO8011, PS8010, column: Wakopak (Wakobeads G-40, G-50) manufactured by Wako Pure Chemical Industries, Ltd., developing solvent: water/methanol/acetic acid/sodium acetate=6/4/0.3/0.41 (weight ratio)) and using polyethylene glycol as a standard substance.
<Measurement of Viscosity>

The copolymer (i) was formed into a 20 wt % aqueous solution, and the viscosity was measured at 25° C. by means of a B-type viscometer and using rotor No. 2 at 30 rpm.

Example 1

(Preparation of Copolymer (i))

Into a reactor equipped with a reflux condenser, a dropping funnel, a thermometer, a nitrogen gas-introducing tube and a stirring device, 200 parts by weight of distilled water was charged, and a monomer mixture solution comprising 43 parts by weight of N-methacryloyloxyethyl-N,N,N-trimethylammonium chloride (DMC) as the cationic vinyl monomer (A), 57 parts by weight of N-hydroxyethylacrylamide (HEAA) as the nonionic vinyl monomer (B) and 100 parts by weight of distilled water, was charged into the dropping funnel. After substitution with nitrogen, the reactor was heated to 90° C. After introducing 0.5 part by weight of 2,2'-azobis(2-methyl-N-(2-hydroxyethyl)-propionamide) into the reactor, the monomer mixture solution was dropwise added from the dropping funnel over a period of 4 hours. After completion of the dropwise addition, the reaction was continued at 90° C. for 20 hours, followed by cooling to obtain a copolymer (i).

Of the obtained copolymer (i), the ratio of the constituting units corresponding to the respective monomers in the total constituting units was DMC/HEAA=43/57 (wt %), the weight average molecular weight was 370,000, the viscosity was 550 mPa·s, the amount of the cationic group was 2.07 meq/g, and the amount of the hydroxy group was 4.95 meq/g.

The results are shown in Table 1.
(Preparation of Hair Wash)

Using the copolymer (i) obtained by the above method, a hair wash having the composition shown in Table 2, was prepared. The numerical values in the Table are weights (parts by weight) of the respective components.
(Evaluation of Cosmetic Composition)

Using the hair wash prepared by the above method, the amount of adsorption of zinc pyrithione on the hair (untreated hair and damaged hair) was measured, and the zinc pyrithione salt persistence was evaluated. The evaluation results are shown in Table 2.

Examples 2 to 6 and Comparative Example 1

(Preparation of Copolymers (ii) to (vii))

Copolymers (ii) to (vii) were, respectively, prepared in the same manner as in the preparation of the copolymer (i) except that monomers disclosed in the monomer compositions in Table 1 were used. The weight average molecular weight, the viscosity, the amount of the cationic group, the amount of the hydroxy group and the amount of the amide group, of the obtained copolymer are shown in Table 1. Here, the ratio of constituting units corresponding to the respective monomers in the total constituting units is the same as the ratio (wt %) of the respective monomers being raw materials for each copolymer shown in Table 1.

Further, one wherein a copolymer (v) was used, is Comparative Example 1.

(Preparation and Evaluation of Hair Wash)

The preparation and evaluation of a hair wash were carried out in the same manner as in Example 1 except that the copolymers (ii) to (vii) were used. The composition and evaluation results of each hair wash are shown in Table 2.

Comparative Example 2

(Preparation and Evaluation of Hair Wash)

The preparation and evaluation of a hair wash were carried out in the same manner as in Example 1 except that cationated hydroxyethylcellulose (JR400, manufactured by Calgon) was used instead of the copolymer (i). The composition and evaluation results of the hair wash are shown in Table 2.

Comparative Example 3

(Preparation and Evaluation of Hair Wash)

The preparation and evaluation of a hair wash were carried out in the same manner as in Example 1 except that a cation-modified guargum (Jaguar C13S, manufactured by Rohm) was used instead of the copolymer (i). The composition and evaluation results of the hair wash are shown in Table 2.

TABLE 1

| | Monomer composition (parts by weight) | | | | | | Weight average molecular weight | Viscosity (mPa·s) | Amount of cationic group (meq/g) | Amount of hydroxy group (meq/g) | Amount of amide group having only nonionic substituent (meq/g) |
|---|---|---|---|---|---|---|---|---|---|---|---|
| | Cationic vinyl monomer (A) | | Nonionic vinylmonomer (B) | | | | | | | | |
| | DMC | DMAPAAC | HEAA | DMAA | GLM | HEMA | | | | | |
| Copolymer (i) | 43 | | 57 | | | | 370,000 | 550 | 2.07 | 4.95 | 4.95 |
| Copolymer (ii) | | 57 | | 43 | | | 300,000 | 890 | 2.76 | 0.00 | 4.34 |
| Copolymer (iii) | 47 | | | | 53 | | 380,000 | 780 | 2.26 | 6.62 | 0.00 |
| Copolymer (iv) | | 47 | | | 53 | | 230,000 | 270 | 2.27 | 6.62 | 0.00 |
| Copolymer (v) | 47 | | | | | 53 | 260,000 | 380 | 2.26 | 4.07 | 0.00 |
| Copolymer (vi) | 47 | | 13 | | 40 | | 325,000 | 645 | 1.93 | 5.78 | 3.91 |
| Copolymer (vii) | 23 | 23 | | 27 | 27 | | 467,000 | 890 | 1.93 | 3.75 | 3.03 |

DMC: N-methacryloyloxyethyl-N,N,N-trimethylammonium chloride
DMAPAAC: N-acryloylaminopropyl-N,N,N-trimethylammonium chloride
HEAA: N-hydroxyethylacrylamide
DMAA: N,N-dimethylacrylamide
GLM: 2,3-dihydroxypropyl methacrylate
HEMA: 2-hydroxyethyl methacrylate

TABLE 2

| | | | Ex. | | | | | | Comp. Ex. | | |
|---|---|---|---|---|---|---|---|---|---|---|---|
| | | Components | 1 | 2 | 3 | 4 | 5 | 6 | 1 | 2 | 3 |
| Cosmetic composition (parts by weight | Copolymer | Copolymer (i) | 0.5 | | | | | | | | |
| | | Copolymer (ii) | | 0.5 | | | | | | | |
| | | Copolymer (iii) | | | 0.5 | | | | | | |
| | | Copolymer (iv) | | | | 0.5 | | | | | |
| | | Copolymer (vi) | | | | | 0.5 | | | | |
| | | Copolymer (vii) | | | | | | 0.5 | | | |
| | | Copolymer (v) | | | | | | | 0.5 | | |
| | Cationated cellulose | Cationated hydroxyethylcellulose | | | | | | | | 0.5 | |
| | Cationated guar | Cation-modified guargum | | | | | | | | | 0.5 |
| | Anion surfactant | Polyoxyethylene(3)lauryl ether sodium sulfate | 9 | 9 | 9 | 9 | 9 | 9 | 9 | 9 | 9 |
| | Amphoteric surfactant | Cocamidepropylbetaine | 5 | 5 | 5 | 5 | 5 | 5 | 5 | 5 | 5 |
| | Nonion surfactant | Cocamidemonoethanolamide | 1 | 1 | 1 | 1 | 1 | 1 | 1 | 1 | 1 |
| | pH-controlling agent | Citric acid | 0.2 | 0.2 | 0.2 | 0.2 | 0.2 | 0.2 | 0.2 | 0.2 | 0.2 |
| | Metal pyrithione salt | Zinc pyrithione | 2 | 2 | 2 | 2 | 2 | 2 | 2 | 2 | 2 |
| | Other | Distilled water | 82.3 | 82.3 | 82.3 | 82.3 | 82.3 | 82.3 | 82.3 | 82.3 | 82.3 |
| | | Sum | 100 | 100 | 100 | 100 | 100 | 100 | 100 | 100 | 100 |

TABLE 2-continued

| | Components | Ex. 1 | Ex. 2 | Ex. 3 | Ex. 4 | Ex. 5 | Ex. 6 | Comp. Ex. 1 | Comp. Ex. 2 | Comp. Ex. 3 |
|---|---|---|---|---|---|---|---|---|---|---|
| Evaluation | Amount of adsorption of zinc pyrithione Untreated hair [μg/g] | 2 | 290 | 174 | 62 | 311 | 342 | 0 | 2 | 0 |
| | Amount of adsorption of zinc pyrithione Damaged hair [μg/g] | 63 | 32 | 83 | 302 | 285 | 257 | 0 | 12 | 6 |

Cationated hydroxyethylcellulose: JR400 (manufactured by Calgon)
Cation-modified guargum: Jaguar C13S (manufactured by Rohm)
Polyoxyethylene(3)lauryl ether sodium sulfate: Stand poll ES-3DS (manufactured by Cofnis)
Cocamidepropylbetaine: AM-3130N (manufactured by Nikko Chemicals Co., Ltd.)
Cocamidemonoethanolamide: Amizole CME (manufactured by Kawaken Fine Chemicals Co., Ltd.)
Zinc pyrithione: Tomicide ZPT50 (Manufactured by API Corporation)

<Evaluation of Results>

1) From the results of the amount of adsorption of zinc pyrithione shown in Table 2, Examples 1 to 4 exhibited high adsorption on the untreated hair or damaged hair. Further, especially, Examples 5 and 6 exhibited high adsorption on both the untreated hair and damaged hair.

2) In Comparative Example 1, zinc pyrithione was not adsorbed on the untreated hair or damaged hair even though N-hydroxyethylmethacrylate was used as a nonionic vinyl monomer for the production of the copolymer.

3) In Comparative Example 2, the zinc pyrithione adsorption on the untreated hair and damaged hair was poor even though a cationated hydroxyethylcellulose was used as a water-soluble resin instead of the copolymer of the present invention.

4) In Comparative Example 3, the zinc pyrithione adsorption on the untreated hair and damaged hair was poor even though a cationated guargum was used as a water-soluble resin instead of the copolymer of the present invention.

INDUSTRIAL APPLICABILITY

The cosmetic composition of the present invention is excellent particularly in the metal pyrithione salt persistence after washing with a washing liquid containing a surfactant, etc., whereby it is possible to exhibit a sufficient anti-dandruff effect by using only a small amount of a metal pyrithione salt.

Particularly in a case where the cosmetic composition of the present invention is used as a washing liquid, it is excellent in both the washing property to remove dirt such as oil or dust on the body, hair or scalp and the anti-dandruff effect, and it is possible to present a washing liquid which exhibits a good touch such as smoothness after the use. Thus, it can be used particularly suitably as a hair wash.

The entire disclosure of Japanese Patent Application No. 2009-038093 filed on Feb. 20, 2009 including specification, claims, drawings and summary is incorporated herein by reference in its entirety.

What is claimed is:

1. A cosmetic composition comprising a copolymer (I) and a metal pyrithione salt, wherein the copolymer comprises constituting units corresponding to a cationic vinyl monomer (A) represented by the following formula (I) and constituting units corresponding to a nonionic vinyl monomer (B) represented by the following formula (II) and/or (III); the proportion of the constituting units corresponding to the cationic vinyl monomer (A) is from 10 to 80 wt % to the total constituting units constituting the copolymer; and the weight average molecular weight of the copolymer is from 10,000 to 2,000,000:

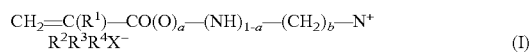

wherein $R^1$ is a hydrogen atom or a methyl group, each of $R^2$ and $R^3$ which are independent of each other, is a $C_{1-24}$ alkyl group, a $C_{1-24}$ aryl group or a $C_{1-24}$ aralkyl group, $R^4$ is a hydrogen atom, a $C_{1-24}$ alkyl group, a $C_{1-24}$ aryl group, a $C_{1-24}$ aralkyl group or $-CH_2-CH(OH)-CH_2-N^+R^5R^6R^7Y^-$, each of $R^5$ to $R^7$ which are independent of one another, is a $C_{1-24}$ alkyl group, a $C_{1-24}$ aryl group or a $C_{1-24}$ aralkyl group, each of $X^-$ and $Y^-$ which are independent of each other, is an anion, a is 0 or 1, and b is an integer of from 1 to 10

wherein $R^8$ is a hydrogen atom or a methyl group, and X is a bivalent linking group containing at least two hydroxy groups

wherein $R^9$ is a hydrogen atom or a methyl group, and each of $R^{10}$ and $R^{11}$ which are independent of each other, is a hydrogen atom, a $C_{1-4}$ alkyl group or a $C_{1-4}$ hydroxyalkyl group; and wherein the amount of the cationic vinyl monomer (A) is from 0.1 to 10.0 meq/g, the amount of nonionic vinyl monomer (B) represented by formula (II) is 1.5 to 20.0 meq/g if present, and the amount of nonionic vinyl monomer (B) represented by formula (III) is 1.5 to 10.0 meq/g if present; and when the cosmetic composition is used as a hair wash, the amount of adsorption of the metal pyrithione salt is at least 20 μg/g on at least one of untreated hair and damaged hair.

2. The cosmetic composition according to claim 1, wherein the metal pyrithione salt is zinc pyrithione.

3. The cosmetic composition according to claim 1, which further comprises an anionic surfactant.

4. The cosmetic composition according to claim 2, which further comprises an anionic surfactant.

5. A hair wash employing the cosmetic composition as defined in claim 1.

6. A hair wash employing the cosmetic composition as defined in claim 2.

7. A hair wash employing the cosmetic composition as defined in claim 3.

8. A hair wash employing the cosmetic composition as defined in claim 4.

* * * * *